United States Patent [19]

Shimada et al.

[11] Patent Number: 5,395,836

[45] Date of Patent: Mar. 7, 1995

[54] 8-TRICYCLOALKYL XANTHINE DERIVATIVES

[75] Inventors: Junichi Shimada, Shizuoka; Takashi Kuwabara, Numazu; Tohru Yasuzawa, Shizuoka; Hiroshi Magara, Shizuoka; Hiromi Nonaka, Shizuoka; Hideaki Kusaka, Shizuoka; Fumio Suzuki, Mishima, all of Japan

[73] Assignee: Kyowa Hakko Kogyo Co., Ltd., Tokyo, Japan

[21] Appl. No.: 222,938

[22] Filed: Apr. 5, 1994

[30] Foreign Application Priority Data

Apr. 7, 1993 [JP] Japan .................................. 5-080841
Dec. 24, 1993 [JP] Japan .................................. 5-327405

[51] Int. Cl.$^6$ .................. C07D 473/04; C07D 473/06; A61K 31/52
[52] U.S. Cl. ................................. 514/263; 544/267; 544/273; 514/869
[58] Field of Search .................. 544/267, 273; 514/263

[56] References Cited

U.S. PATENT DOCUMENTS

| | | | |
|---|---|---|---|
| 4,233,303 | 11/1980 | Bergstrand et al. | 424/253 |
| 4,755,517 | 7/1988 | Bruns et al. | 514/263 |
| 5,290,782 | 3/1994 | Suzuki et al. | 514/263 |
| 5,342,841 | 8/1994 | Suzuki | 544/267 |

FOREIGN PATENT DOCUMENTS

| | | |
|---|---|---|
| 0414175 | 2/1991 | European Pat. Off. |
| 0497258 | 8/1992 | European Pat. Off. |
| 0541120 | 5/1993 | European Pat. Off. |
| 4-270222 | 9/1992 | Japan . |
| 560354 | 9/1993 | Japan .................................. 544/267 |

OTHER PUBLICATIONS

Patent Abstracts of Japan, vol. 17, No. 63 (Feb. 8, 1993) (C-1024), for JP 4-270222.

Henin et al., Tetrahedron Letters, vol. 27, No. 52 (1986) 6339–40.

Primary Examiner—Mark L. Berch
Attorney, Agent, or Firm—Fitzpatrick, Cella, Harper & Scinto

[57] ABSTRACT

There is provided a novel xanthine Compound(I)

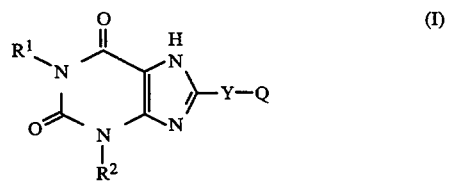

wherein $R^1$ and $R^2$ are the same or different and each represent hydroxy-substituted, oxo-substituted or unsubstituted lower alkyl, Y is a single bond or alkylene, and Q is

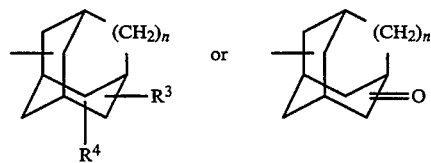

wherein $R^3$ and $R^4$ are the same or different and each represent hydrogen or hydroxy, n is 0 or 1; provided that when both of $R^3$ and $R^4$ are hydrogen, at least one of $R^1$ and $R^2$ is hydroxy-substituted or oxo-substituted lower alkyl; or a pharmaceutically acceptable salt thereof.

The xanthine compound has adenosine $A_1$ receptor antagonizing activity, and thus shows diuretic effect, renal-protecting effect, bronchodilatory effect, cerebral function improving effect and anti-dementia effect.

6 Claims, No Drawings

8-TRICYCLOALKYL XANTHINE DERIVATIVES

BACKGROUND OF THE INVENTION

The present invention relates to xanthine derivatives or pharmaceutically acceptable salts thereof having adenosine $A_1$ receptor antagonizing activity, and thus exhibiting diuretic effect, renal-protecting effect, bronchodilatory effect, cerebral function improving effect, and anti-dementia effect.

In relation to the compounds of the present invention, 8-(1-adamantyl)-1,3,7-trimethylxanthine is disclosed in Tetrahedron Letters, 27, 6339–6340 (1986). However, nothing is mentioned on its pharmacological effect in the literature.

Also, it is known that a xanthine derivative represented by the formula

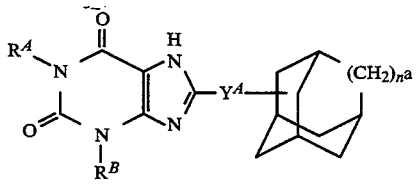

(wherein $R^A$ and $R^B$ are lower alkyl, $Y^A$ is a single bond or alkylene, and $n^a$ is 0 or 1) has activity of selectively antagonizing adenosine $A_1$ receptor and thus shows renal-protecting effect, and bronchodilatory effect (Japanese Published Unexamined Patent Application No. 173889/91); and cerebral function improving effect (Japanese Published Unexamined Patent Application No. 270222/92). Further, it is known that a xanthine derivative represented by the formula

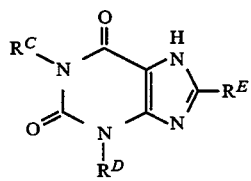

(wherein $R^C$ and $R^D$ are hydroxy-substituted or unsubstituted lower alkyl, and $R^E$ is substituted or unsubstituted tricycloalkyl of $C_7$–$C_{12}$) shows anti-ulcerative effect, etc. (Japanese Published Unexamined Patent Application No. 58913/93), but no specific examples of the hydroxy-substituted xanthine derivatives are disclosed in the publication.

It is also known that a xanthine derivative represented by the formula

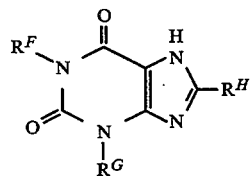

(wherein, $R^F$ and $R^G$ are the same or different, and each represent hydroxy-substituted or unsubstituted lower alkyl, and $R^H$ is dihydroxyalkyl or

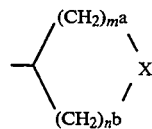

[wherein, X is O, S or $NR^P$ (wherein $R^P$ is hydrogen, lower alkyl or lower acyl), $m^a$ and $n^b$ are the same or different and each represent an integer of from 1 to 5] shows central nervous system stimulating effect (U.S. Pat. No. 4,755,517). It is known that a xanthine derivative represented by the formula

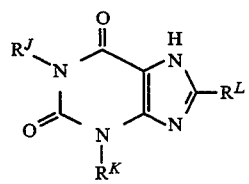

(wherein, $R^J$ is methyl, ethyl or propyl, $R^K$ is 2-hydroxypropyl, and $R^L$ is methyl or propyl) shows antiallergic effect (Japanese Published Unexamined Patent Application No. 79296/79) and that a xanthine derivative represented by the formula

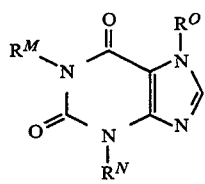

[wherein at least one of $R^M$ and $R^O$ is ($\omega-1$)-hydroxyalkyl having from three to eight carbon atoms, or when only one of $R^M$ and $R^O$ is ($\omega-1$)-hydroxyalkyl, the other is hydrogen or lower alkyl, and $R^N$ is lower alkyl] has activity of reducing nephrotoxicity (Japanese Published Unexamined Patent Application No. 90028/91).

SUMMARY OF THE INVENTION

An object of the present invention is to provide a xanthine derivative and a pharmaceutically acceptable salt thereof having adenosine $A_1$ receptor antagonizing activity and thus exhibiting diuretic effect, renal-protecting effect, bronchodilatory effect, cerebral function improving effect and anti-dementia effect.

In accordance with the present invention, there is provided a xanthine derivative represented by the formula (I) [which is hereinafter referred to as Compound (I) and the same applies to the compounds of other formula numbers]

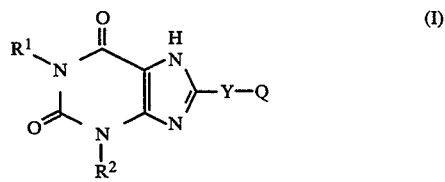

[wherein $R^1$ and $R^2$ are the same or different and each represent hydroxy-substituted, oxo-substituted or unsubstituted lower alkyl, Y is a single bond or alkylene, and Q is

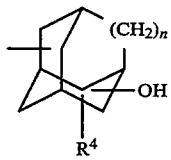

(wherein $R^3$ and $R^4$ are the same or different and each represent hydrogen or hydroxy, n is 0 or 1, and when both $R^3$ and $R^4$ are hydrogen, at least one of $R^1$ and $R^2$ is hydroxy-substituted or oxo-substituted lower alkyl), or

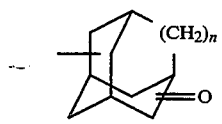

(wherein n has the same meaning as defined above)] or a pharmaceutically acceptable salt thereof.

In the definition of Compound (I), the lower alkyl means a straight or branched alkyl having 1 to 6 carbon atoms, such as methyl, ethyl, propyl, isopropyl, butyl, isobutyl, sec-butyl, tert-butyl, pentyl and hexyl; and the alkylene means a straight or branched alkylene having 1 to 4 carbon atoms such as methylene, ethylene, trimethylene, tetramethylene, methylmethylene, propylene, ethylethylene and the like. Each of $R^1$ and $R^2$ is optionally substituted with one to 2 substituents which is/are independently selected from the group consisting of hydroxy and oxygen. As the preferred example of $R^1$ and $R^2$, mention may be made of 2- or 3- hydroxy-substituted propyl; 2- or 3- oxo-substituted propyl; and unsubstituted propyl. In the definition of Q, as the site where Q is bonded to Y, any position can be selected arbitrarily, and hydroxy and oxygen as the substituent can be situated in any position. A preferred example of Q includes 3-tricyclo[3.3.1.0$^{3,7}$]nonyl which is optionally substituted by hydroxy or oxygen at the 9-position or 6-position, and 1-tricyclo[3.3.1.1$^{3,7}$]decyl which is optionally substituted by hydroxy or oxygen at the 3-position.

The pharmaceutically acceptable salts of Compound (I) include pharmaceutically acceptable acid addition salts, pharmaceutically acceptable metal salts, pharmaceutically acceptable ammonium salts, pharmaceutically acceptable organic amine addition salts, and pharmaceutically acceptable amino acid addition salts.

The pharmaceutically acceptable acid addition salt of Compound (I) includes inorganic acid addition salts such as hydrochloride, sulfate and phosphate; and organic acid addition salts such as acetate, maleate, fumarate, tartrate and citrate. The pharmaceutically acceptable metal salt includes alkali metal salts such as sodium salt and potassium salt, alkaline earth metal salts such as magnesium salt and calcium salt, as well as aluminium salt and zinc salt. The pharmaceutically acceptable ammonium salt includes ammonium salt and tetramethyl ammonium salt. The pharmaceutically acceptable organic amine addition salt includes salts with morpholine and piperidine, and pharmaceutically acceptable amino acid addition salt includes salts with lysine, glycine and phenylalanine.

The processes for preparing Compound (I) are described as follows.

Preparation Process 1:

Compound (I) can be prepared by the following reaction steps:

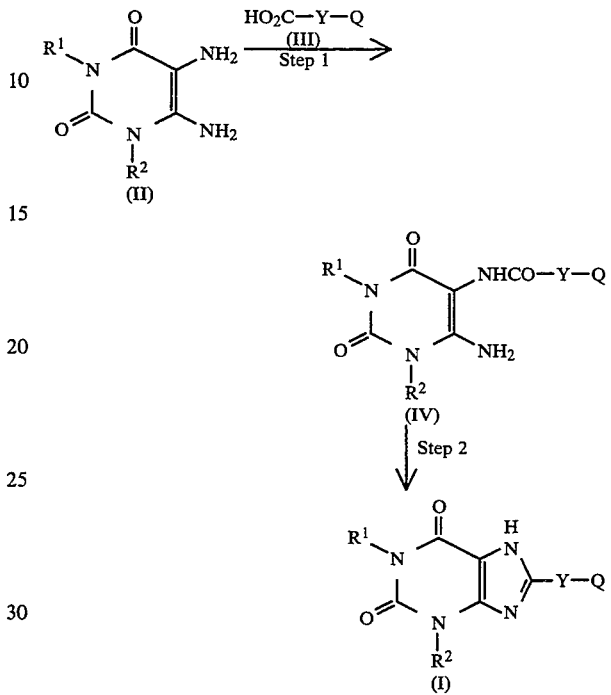

(wherein, $R^1$, $R^2$, Y and Q have the same meanings as defined above.)

Step 1

Compound (IV) can be obtained by reacting an uracil derivative (II) obtained by a known method, for example, the method as disclosed in Japanese Published Unexamined Patent Application No. 79296/79, with a carboxylic acid (III) or a reactive derivative thereof.

As for the carboxylic acid (III) wherein n is 1, it can be prepared by the method as described in the following.

3-Hydroxyadamantane-1-carboxylic acid: Syn. Commun., 18, 1967 (1988).

2-Hydroxyadamantane-1-carboxylic acid and 4-hydroxy adamantane-1-carboxylic acid: J. Org. Chem., 38, 3447 (1973).

2-Oxoadamantane-1-carboxylic acid: J. Chem. Soc. Perkin I, 1893 (1976).

4-Oxoadamantane-1-carboxylic acid: J. Org. Chem., 48, 1099 (1973).

As for the carboxylic acid (III) wherein n is 0, it can be prepared by the method as described in the following.

9-Hydroxytricyclo[3.3.1.0$^{3,7}$]nonane-3-carboxylic acid (9-hydroxynoradamantane-3-carboxylic acid): J. Chem. Soc. Perkin I, 1669 (1973).

1-Hydroxytricyclo[3.3.1.0$^{3,7}$]nonane-3-carboxylic acid: J. Org. Chem., 48, 5231 (1983).

2-Hydroxytricyclo[3.3.1.0$^{3,7}$]nonane-2-carboxylic acid: Synthesis, 74 (1980).

9-Oxotricyclo[3.3.1.0$^{3,7}$]nonane-3-carboxylic acid: Chem. Ber., 103, 863 (1970).

9-Oxotricyclo[3.3.1.0$^{3,7}$]nonane-1-carboxylic acid: J. Am. Chem. Soc., 113, 6607 (1991).

6-Oxotricyclo[3.3.1.0³,⁷]nonane-3-carboxylic acid is a new compound, which is prepared by a process shown in Reference example hereinafter.

As the reactive derivative of Compound (III), mention may be made of acid halides such as acid chloride and acid bromide; active esters such as p-nitrophenylester and N-oxysuccinimide; commercially available acid anhydrides or acid anhydrides produced by the use of carbodiimide such as 3-(3-dimethylaminopropyl)-1-ethylcarbodiimide, diisopropylcarbodiimide and dicyclohexylcarbodiimide; and acid anhydrides mixed with carbonic acid monoethyl ester and carbonic acid monoisobutyl ester and the like.

The reaction, wherein Compound (III) is used, is carried out at 50° to 200° C. in the absence of a solvent, and completed in 10 minutes to 5 hours.

The reaction, wherein a reactive derivative of Compound (III) is used, is carried out by a method similar to those generally used in peptide chemistry. That is, Compound (IV) can be obtained by reacting Compound (II) with a reactive derivative of Compound (III), preferably in the presence of an additive or a base. As the reacting solvent, mention may be made of halogenated hydrocarbons such as methylene chloride, chloroform and ethylene dichloride; ethers such as dioxane and tetrahydrofuran; dimethylformamide and dimethylsulfoxide, and if necessary water and the like. The additive is exemplified by 1-hydroxybenzotriazole and the like. The base is exemplified by pyridine, triethylamine, 4-dimethylaminopyridine, N-methylmorpholine and the like. The reaction is carried out at −80° to 50° C. and completed in 30 minutes to 24 hours. The reactive derivative can be used as such without isolation after it has been produced in the reaction system.

Step 2

Compound (I) can be obtained by treating Compound (IV) with a base (method A), by treating Compound (IV) with a dehydrating agent (method B) or by heating Compound (IV) (method C).

In the method A, as the base, mention may be made of an alkali metal hydroxide such as sodium hydroxide and potassium hydroxide and an alkaline earth metal hydroxide such as calcium hydroxide. As the reaction solvent, water, a lower alcohol such as methanol and ethanol, an ether such as dioxane and tetrahydrofuran, dimethylformamide, dimethylsulfoxide and the like may be used alone or in combination. The reaction is carried out at 0° to 180° C. and completed in 10 minutes to 6 hours.

In the method B, as the dehydrating agent, mention may be made of thionyl halide such as thionyl chloride, and phosphorus oxyhalide such as phosphorus oxychloride. The reaction is carried out in the absence of a solvent or in the presence of an inert solvent such as halogenated hydrocarbons (e.g. methylene chloride, chloroform and ethane dichloride), dimethylformamide and dimethylsulfoxide, at 0° to 180° C. and in 30 minutes to 12 hours.

In the method C, a polar solvent such as dimethylformamide, dimethylsulfoxide and Dow Thermo A (available from The Dow Chemical Co.) is used as the reaction solvent. The reaction is carried out at 50° to 200° C. and completed in 10 minutes to 5 hours.

Preparation Process 2:

Compound (I) can be prepared by the following reaction process.

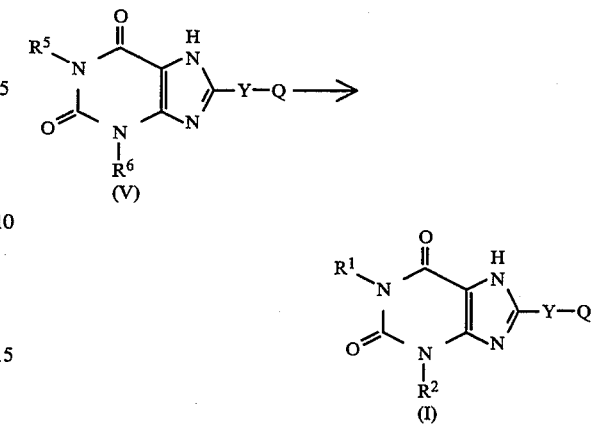

(wherein at least one of $R^5$ and $R^6$ is lower alkenyl, the other is lower alkyl and $R^1$, $R^2$, Y and Q have the same meanings as defined above).

The lower alkenyl as used herein means a straight or branched alkenyl having 2 to 6 carbon atoms, such as vinyl, allyl, propenyl, isopropenyl, butenyl and hexenyl, and the lower alkyl has the same meaning as defined above.

Compound (I) can be obtained by hydrating or oxidizing Compound (V) obtained by the above-mentioned Preparation Process 1, or according to the known method as described in Japanese Published Unexamined Patent Application No. 173889/91) or a method similar thereto. The hydration reaction can be carried out by the following four methods.

Method A: Compound (I) can be obtained by heating Compound (V) in a proton acid at 80° to 120° C. for 1 to 4 days. As the proton acid, dilute sulfuric acid, dilute nitric acid and aqueous perchloric acid and the like can be used.

Method B: Compound (I) can be obtained by hydroborating Compound (V), followed by oxidation. Examples of the hydroborating agent are diborane ($B_2H_6$), its complex (e.g. tetrahydrofuran complex, dimethylsulfide complex, triethylamine complex and the like), diisoamylborane, thexylboran, 9-borabicyclo[3.3.1]nonane(9-BBN) and the like. As the reaction solvent, ethers such as diglyme, tetrahydrofuran and diethyl ether can be used. The reaction is carried out at −30° to 50° C. and completed in 10 minutes to 12 hours. The oxidation reaction can be carried out by treating hydroborated Compound (I) with aqueous hydrogen peroxide in a mixed solvent of ethers such as diglyme, tetrahydrofuran and diethyl ether and an alkali aqueous solution at 0° to 50° C. for 10 minutes to 4 hours.

Method C: Compound (I) can be obtained by subjecting Compound (V) to the oxymercuration reaction with mercuric acetate and the like, followed by treatment with an alkali borohydride such as sodium borohydride. In the oxymercuration reaction, a mixed solvent of water; and one of acetone, an ether and tetrahydrofuran is used as the solvent. The reaction is carried out at 0° to 50° C. and completed in 10 minutes to 12 hours. After the oxymercuration reaction is completed, the reaction mixture is alkalized, and reacted with an alkali metal borohydride at 0° to 30° C. for 10 minutes to 12 hours to produce Compound (I).

Method D: Compound (I) can be obtained by treating Compound (V) in the presence of a catalytic amount of palladium, with a re-oxidizing agent, in an oxygen atmosphere. Examples of the palladium catalyst include palladium chloride, bis(acetonitrile)palladium chloride, palladium sulfate, and bis(acetonitrile)nitropalladium chloride. Examples of the re-oxidizing agent are cuprous chloride, cupric chloride, cuptic nitrate, cupric acetate or p-benzoquinone and the like. As the reaction solvent, ethers such as dioxane and tetrahydrofuran, dimethylformamide and water can be used alone or in combination. The reaction is carried out at 0° to 180° C. and completed in 10 minutes to 24 hours.

Preparation Process 3:

Compound (I-1), which is Compound (I) wherein Q is

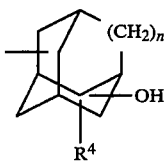

(in which $R^4$ and n are previously defined), or

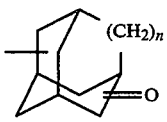

(wherein n is previously defined), can be produced by the following reaction process.

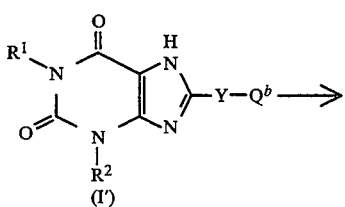

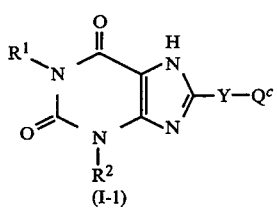

[wherein $Q^b$ is a group in the definition of Q, represented by the following formula

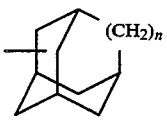

(wherein n is previously defined); $Q^c$ is a group in the definition of Q, represented by the following formula

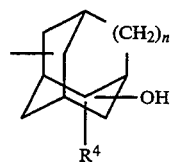

(wherein $R^4$ and n are previously defined) or a group in the definition of Q, represented by the following formula

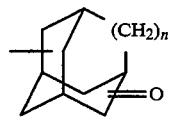

(wherein n is previously defined), and $R^1$, $R^2$ and Y are previously defined].

Method A: Compound (I-1) can be obtained by subjecting Compound (I') to regio- or stereospecific hydroxylation or carbonylation in the presence of an appropriate oxidizing agent.

The oxidizing agent includes, for example, chromic anhydride, potassium permanganate, aqueous hydrogen peroxide, oxygen, ozone, nitric acid or organic peroxides such as tert-butyl hydroperoxide and dimethyl dioxirane. Further, ferrous chloride, ferric chloride, ferrous sulfate, ruthenium chloride and the like can be added, if necessary. The reaction solvent, depending on the sort of the oxidizing agent to be used, includes water, acetic acid, acetic anhydride, pyridine, benzene, acetonitrile and the like. The reaction is carried out at −50° to 150° C. and completed in 10 minutes to 96 hours.

Method B: Compound (I-1) can be obtained by suspending hepatocyte microsome obtained by the known method as described in Tetsuya Kamataki et al., (1985) "Applied Pharmacokinetics, Theory and Experiments" p.325, Edited by Manabu Hanano et al., Soft Science Co., Tokyo, in a neutral phosphate buffer, adding dihydronicotinamide adenine dinucleotide phosphate (NADPH) or an NADPH-generating reaction system thereto, and incubating the resulting mixture together with Compound (I') preferably in the presence of bovine serum albumin and a stabilizing agent.

As the hepatocyte microsome, that derived from a rat to which an inducer of a drug metabolic enzyme such as Phenobarbital Sodium have been administered, is preferably employed. The NADPH-generating system is not specifically limited, and an example is a mixed solution of 8 mM sodium β-nicotinamide adenine dinucleotide phosphate (β-NADP), 80 mM sodium glucose-6-phosphate, 10 units of glucose 6-phosphate dehydrogenase (derived from yeast; Oriental Yeast Co., Ltd.) and 60 mM magnesium chloride. As the stabilizing agent, any agent which can inhibit the lipid peroxidation of the hepatocyte microsome to stabilize the drug metabolic enzyme can be used, and one example is disodium ethylenediamine tetraacetate (EDTA). The incubation is carried out at 30° to 40° C., preferably at 37° C. and the reaction is completed in 10 minutes to 24 hours.

Preparation Process 4:

Compound (I-1) can also be prepared by the following reaction steps.

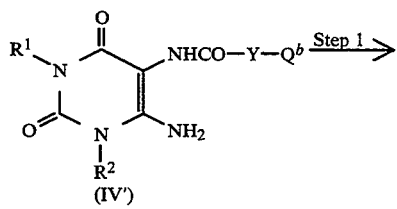

(IV')

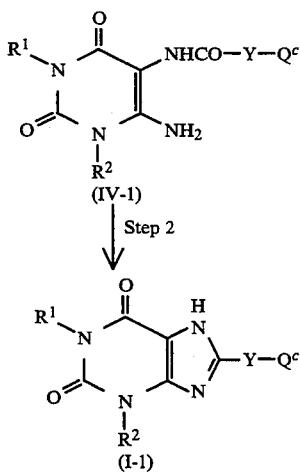

(wherein R¹, R², Y Q$^b$ and Q$^c$ have the same meanings as defined above)

Step 1

Compound (IV') prepared by a method similar to the Preparation Process 1—Step 1 is subjected to an oxidation reaction similar to that described in Preparation Process 3 to provide Compound (IV-1), which is Compound (IV) in which Q is Q$^c$].

Step 2

Compound (I-1) is obtained by cyclizing Compound (IV-1) in a manner similar to that described in Preparation Process 1—Step 2.

The desired compounds in the processes described above can be isolated and purified by purification methods conventionally used in organic synthetic chemistry such as filtration, extraction, washing, drying, concentration, recrystallization and various kinds of chromatography.

In the case where a salt of Compound (I) is desired, and it is produced in the form of the desired salt, the product as such can be subjected to purification. In the case where Compound (I) is produced in the free form and its salt is desired, Compound (I) is dissolved or suspended in a suitable solvent, followed by addition of an acid or a base to form a salt.

Compound (I) and the pharmaceutically acceptable salt thereof may also be in the form of adducts with water or various solvents, and the addition products are within the scope of this invention.

Compound (I) can exist in the form of optical isomers and the present invention covers all possible stereoisomers and mixtures thereof.

Representative examples of Compound (I) are shown in Table 1.

TABLE 1

| Compound | R¹ | R² | Q |
|---|---|---|---|
| 1 | n-C$_3$H$_7$ | n-C$_3$H$_7$ | |
| 2 | n-C$_3$H$_7$ | n-C$_3$H$_7$ | |
| 3 | n-C$_3$H$_7$ | n-C$_3$H$_7$ | |

TABLE 1-continued

| Compound | R¹ | R² | Q |
|---|---|---|---|
| 4 | n-C$_3$H$_7$ | n-C$_3$H$_7$ | (tricyclic group with H, OH) |
| 5 | n-C$_3$H$_7$ | n-C$_3$H$_7$ | (tricyclic group with H, OH, different stereochemistry) |
| 6 | n-C$_3$H$_7$ | HOCH$_2$CH$_2$CH$_2$— | (tricyclic group) |
| 7 | n-C$_3$H$_7$ | CH$_3$CH(OH)CH$_2$— | (tricyclic group) |
| 8 | n-C$_3$H$_7$ | n-C$_3$H$_7$ | (tricyclic group with OH) |
| 9 | CH$_3$C(=O)CH$_2$— | n-C$_3$H$_7$ | (tricyclic group) |
| 10 | CH$_3$CH(OH)CH$_2$— | n-C$_3$H$_7$ | (tricyclic group) |

TABLE 1-continued
[Structure shown: xanthine core with R¹ on N1, R² on N3, Q on C8 of imidazole ring]
| Compound | R¹ | R² | Q |
|---|---|---|---|
| 11 | O=CHCH₂CH₂— | n-C₃H₇ | 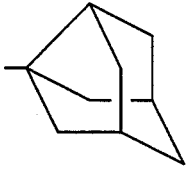 |
| 12 | CH₃C(=O)CH₂— | n-C₃H₇ | 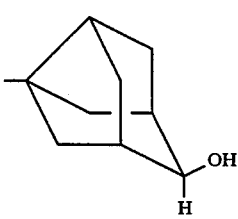 |
| 13 | CH₃CH(OH)CH₂— | n-C₃H₇ | 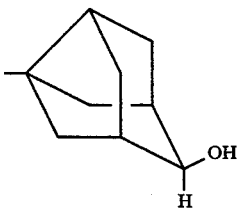 |
| 14 | CH₃C(=O)CH₂— | n-C₃H₇ | 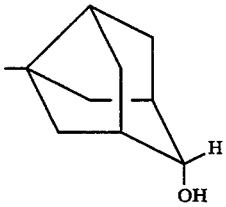 |
| 15 | CH₃CH(OH)CH₂— | n-C₃H₇ | 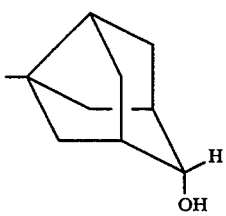 |
| 16 | CH₃C(=O)CH₂— | n-C₃H₇ | 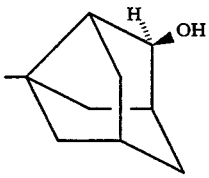 |

TABLE 1-continued

| Compound | R¹ | R² | Q |
|---|---|---|---|
| 17 | CH$_3$CH(OH)CH$_2$— | n-C$_3$H$_7$ | (noradamantanyl-OH) |

Compound (I) and the pharmaceutically acceptable salt thereof have adenosine A$_1$ antagonizing activity, and thus exhibit diuretic effect, and renal-protecting effect, and anti-dementia effect. Compounds (I) and the pharmaceutically acceptable salts thereof are expected to be useful as a diuretic agent, a hypotensive agent and an anti-edematous agent with diuretic effect, as well as a renal-protecting agent to prevent and treat nephrotoxicity, to protect renal function, to prevent and treat nephritis, and to prevent and treat nephrotic syndrome.

Compound (I) and the pharmaceutically acceptable salt thereof further show bronchodilatory effect, cerebral function improving effect and anti-dementia effect.

The pharmacological activities of Compound (I) are illustrated by the following test examples.

Test Example 1

Acute Toxicity Test

Test compounds Nos. 1 to 17 were orally administered to groups of dd-strain male mice weighing 20±1 g, each group consisting of three mice. Seven days after the administration, minimum lethal dose (MLD) of each compound was determined by observing the mortality.

Test compounds Nos. 1 to 17 showed MLD of >300 mg/kg, and thus can be safely used in a wide range of doses.

Test Example 2

Adenosine Receptor Antagonizing Activity (Adenosine A$_1$ Receptor Binding Test)

The test was conducted according to the method of Bruns et al. [Proc. Natl. Acad. Sci. U.S.A., 77., 5547 (1980)] with slight modification.

Corpus striatum of a rat was suspended in ice-cooled 50 mM Tris hydroxymethyl aminomethane hydrochloride (Tris HCl) buffer (pH 7.7) by using Polytron homogenizer (manufactured by Kinematicas Co.). The suspension was centrifuged (50,000×g, 10 minutes), and the precipitate was suspended again in the same amount of 50 mM Tris HCl buffer. The suspension was centrifuged under the same conditions, and the final precipitate was suspended once again in 50 mM Tris HCl buffer to give a tissue concentration of 100 mg (wet weight)/ml. The tissue suspension was allowed to stand in the presence of 0.02 unit/mg tissue of adenosine deaminase (manufacture by Sigma Co.) at 37° C. for 30 minutes. The tissue suspension was centrifuged (50,000×g, 10 minutes) and to the obtained precipitates was added 50 mM Tris HCl buffer to give a tissue concentration of 10 mg (wet weight)/ml.

To 1 ml of the tissue suspension thus prepared, were added 50 μl of cyclohexyladenosine labeled with tritium ($^3$H-CHA: 27 Ci/mmol, manufactured by New England Nuclear) (final concentration: 1.1 nM), and 50 μl of a test compound. The resulting mixture was allowed to stand at 25° C. for 90 minutes and then rapidly filtered by suction through a glass fiber filter (GF/C, manufactured by Whatman Co.). The filter was immediately washed three times with 5 ml each of ice-cooled 50 mM Tris HCl buffer, and transferred to a vial, and scintillator (EX-H by Wako Pure Chemical Industries, Ltd.) was added thereto. The radioactivity on the filter was determined with a liquid scintillation counter (manufactured by Packard Instrument Co.).

The inhibition rate (Ki value) of the test compound against the binding of A$_1$ receptors ($^3$H-CHA binding) was calculated by the equation of Cheng-Prusoff.

$$\text{Inhibition Rate (\%)} = \left(1 \times \frac{[B] - [N]}{[T] - [N]}\right) \times 100$$

[Notes]

1. "B" means the amount of radioactivity of $^3$H-CHA bound in the presence of a test compound at various concentrations.

2. "T" means the amount of radioactivity of $^3$H-CHA bound in the absence of a test compound.

3. "N" means the amount of radioactivity of $^3$H-CHA bound in the presence of 10 μM N$^6$-(L-2-phenylisopropyl)adenosine (Sigma Co.).

TABLE 2

| Test Compound | Ki (nM) |
|---|---|
| 1 | 0.37 |
| 2 | 0.59 |
| 3 | 0.23 |
| 4 | 0.31 |
| 5 | 0.24 |
| 6 | 0.96 |
| 7 | 6.1 |
| 8 | 5.1 |

Test Example 3

Diuretic Effect

The experiment was performed by using Wistar rats (male; 150 to 300 g). The rats were starved for 18 hours prior to the administration of a test compound (n=4 to 5). After test compounds were dissolved in 0.4% methanol, 1% dimethylsulfoxide and 0.01N sodium hydroxide/physiological saline, and administered intravenously, the physiological saline (25 ml/kg) was orally administered. Alternatively, test compounds dissolved in the physiological saline (25 ml/kg) was orally administered to the rats. Urine was collected from the rats during 4 hours after the oral administration, and urine volume was measured by a graduated measuring cylinder, and the electrolytes in the urine ($Na^+$ and $K^+$) were determined by flame photometer (775 A manufactured by Hitachi, Ltd.). The results are shown in Tables 3 and 4.

TABLE 3

| Test Compound | Dose (μg/kg, iv) (n = 5) | Amount of urine (ml/kg) | Amount of $Na^+$ excreted (mEq/kg) | Amount of $K^+$ excreted (mEq/kg) | $Na^+/K^+$ |
|---|---|---|---|---|---|
| Control group | — | 14.5 ± 1.8 | 2.23 ± 0.61 | 1.47 ± 0.31 | 1.52 |
| 3 | 3 | 26.4 ± 0.6** | 3.71 ± 0.12* | 1.24 ± 0.10 | 2.99 |

*p < 0.05; **p < 0.01 (Dunnett's test)

TABLE 4

| Test Compound | Dose (mg/kg, po) (n) | Increase in amount of urine Δ(%) | Increase in amount of $Na^+$ excreted Δ(%) | Increase in amount of $K^+$ excreted Δ(%) | $Na^+/K^+$ |
|---|---|---|---|---|---|
| Control Group | —(4~5) | 0 | 0 | 0 | 1.00 |
| 1 | 0.01(5) | 149 | 144 | 37 | 1.78 |
| 1 | 1.6(5) | 258 | 193 | 36 | 2.15 |
| 2 | 0.1(5) | 211 | 177 | 32 | 2.10 |
| 2 | 1.6(5) | 241 | 188 | 8 | 2.67 |
| 3 | 0.01(4) | 99 | 139 | 11 | 2.16 |
| 3 | 0.1(4) | 105 | 148 | −9 | 2.72 |
| 4 | 0.01(5) | 200 | 167 | 43 | 1.86 |
| 4 | 1.6(5) | 232 | 180 | 35 | 2.07 |
| 5 | 0.1(5) | 134 | 107 | 12 | 1.85 |
| 5 | 1.6(5) | 297 | 220 | 15 | 2.77 |
| 6 | 0.025(5) | 134 | 111 | 5.1 | 2.00 |
| 6 | 0.1(5) | 396 | 276 | 24 | 3.03 |
| 7 | 0.01(5) | 140 | 97 | 33 | 1.48 |
| 7 | 0.1(5) | 200 | 138 | 23 | 1.93 |

From Tables 3 and 4, test compounds were found to have high Na-diuretic effect.

Test Example 4

Renal-protecting Effect (Glycerol-Induced Renal Failure Model)

A renal failure is a state where the renal function is lowered and the homeostasis of a body fluid can be no longer maintained. It is known that an acute renal failure characteristic of uriniferous tubule disorder is caused by subcutaneous or intramuscular injection of glycerol to rats [Can. J. Physiol. Pharmacol., 65, 42 (1987)].

Male Wistar rats were kept deprived of water for 18 hours, and served for the test. A test compound was intraperitoneally administered to the rats (dosage: 0.1 ml/100 g). After 30 minutes, the rats were anesthetized with ether and 50% glycerol was subcutaneously administered (dosage: 0.8 ml/100 g) to the rats, pinching the dorsal skin. Twenty four hours after the administration of glycerol, the rats were anesthetized with ether and 5 ml of blood was collected from the abdominal aorta. The collected blood was allowed to stand for 30 minutes or longer and then centrifuged at 3,000 rpm for 10 minutes, and the amounts of the serum creatinine and the serum urine-nitrogen (UN) were determined by auto analyzer (Olympus AU510) [creatinine test (Jaffé method), UN test (enzyme method); both tests were used in Olympus AU500/550 exclusive reagent KATAYAMA.

The test results were treated statistically [test of significance, Student's t-test (n=8~10)] between the control groups and the test compound-administered groups. The results are shown in Table 5.

TABLE 5

| Test Compound | Dose (mg/kg, ip) | Amount of creatinine in blood serum (mg/dl) | Amount of uria nitrogen in blood serum (mg/dl) |
|---|---|---|---|
| Control group | — | 4.55 ± 0.24 | 137.2 ± 5.0 |
| 1 | 0.03 | 2.51 ± 0.41*** | 81.4 ± 15.9*[1)] |
| 2 | 0.03 | 2.51 ± 0.24*** | 85.0 ± 8.7*** |
| 4 | 0.03 | 2.32 ± 0.48** | 75.6 ± 13.9**[1)] |
| 5 | 0.1 | 2.34 ± 0.24*** | 74.4 ± 7.7*** |
| Control group | — | 3.90 ± 0.24 | 124.9 ± 7.5 |
| 6 | 0.01 | 2.23 ± 0.15*** | 65.4 ± 5.6*** |
| 7 | 0.01 | 2.28 ± 0.22*** | 70.0 ± 9.8*** |
| Control group | — | 4.35 ± 0.23 | 139.7 ± 10.2 |
| 3 | 0.01 | 2.00 ± 0.21**[2)] | 69.9 ± 8.4**[2)] |
| 3 | 0.1 | 2.32 ± 0.16[2)] | 64.4 ± 4.5[2)] | p < 0.01; *p < 0.001 (Student's t test); [1)]p < 0.01 (Aspin-Welch test); [2)]p < 0.01 (Dunnett's test)

Table 5 showed that test compounds administered intraperitoneally at a dose of 0.1 mg/kg or lower, significantly inhibited the increase in the amount of creatinine and that in the amount of urea nitrogen in blood serum.

On the contrary, aminophylline (10 mg/kg, i.p.) showed a weak effect of suppressing the increase, and furosemide (10 mg/kg, i.p.) showed a tendency to increase the serum creatinine.

Test Example 5

Activity on (R)-PIA-Induced Amnesia

Anti-dementia effect of Compound (I) was determined with (R)-PIA[(R)-$N^6$-(2-phenylisopropyl)adenosine]-induced dementia model [Jpn. J. Pharmacol. 52 (Suppl. II), 107P (1990)] As the experimental animal, groups of ddY-strain mice (weighing 20–25 g), each group consisting of fifteen mice, were used. The test was performed with a step-through type passive avoidance apparatus (the bright and dark box).

The bright and dark box was made up of a bright compartment (15×9×11 cm) lighted by 4 W white fluorescent light and a dark compartment (15×14×18 cm). These two compartments were partitioned by a guillotine door (3×3 cm) and had a grid floor of stainless steel. In order to give a foot shock, the electric current (0.3 mA: 2 sec) may be passed through the grid floor of the dark compartment.

The compound to be tested was suspended in 0.3% aqueous solution of carboxymethyl cellulose (CMC) and the suspension was orally administered 60 minutes before the acquisition trial (to the normal control group and the amnesia control group which is subjected to the following amnesia treatment, only 0.3% CMC was administered). 30 minutes after the administration of the test compound, 0.3 mg/kg of (R)-PIA was administered intraperitoneally as amnesia-inducing treatment [(R)-PIA was not administered to the normal control group].

The training for acquisition of learning (acquisition trial) was carried out. The rat was introduced into the bright compartment, and after 10 seconds, the guillotine door was opened. The rat in the bright compartment rapidly moved into the dark compartment. As soon as the whole body of the rat entered the dark compartment, the guillotine door was closed and an electric current of 0.3 mA was passed through the grid floor for 2 seconds (foot shock). Immediately after the foot shock, the rat was taken out of the dark compartment.

The test trial for observing the retention and recall of the memory (recall trial) was carried out as follows. Twenty-four hours after the acquisition trial, the rat was placed in the bright compartment and the guillotine door was opened. The length of time before the rat entered the dark compartment (latency) was measured. The latency was measured up to 600 seconds and the latency longer than 600 seconds was recorded as 600 seconds.

The anti-dementia effect was judged from whether or not the reaction latency of the test compound-administered group was significantly increased from the reaction latency of the amnesia control group. The test of significance was carried out by Steel-test. The results are shown in Table 6.

TABLE 6

| Test Compound | Dose (mg/kg; oral) | Amnesia treatment | Number of used animals | Recall trial average reaction latency (sec) | Comparison with amnesia control |
|---|---|---|---|---|---|
| normal control | — | — | 15 | 560.0 ± 26.6 | — |
| amnesia control | — | + | 15 | 51.5 ± 17.0 | — |
| Compound 3 | 0.08 | + | 15 | 404.3 ± 43.5 | p < 0.01 |
|  | 0.31 | + | 15 | 438.8 ± 43.0 | p < 0.01 |
|  | 1.25 | + | 15 | 445.5 ± 49.5 | p < 0.01 |
|  | 5.0 | + | 15 | 430.5 ± 43.2 | p < 0.01 |

As seen from Table 6, an oral administration of Compound (I) at a dose of 5 mg/kg or lower exhibited anti-dementia effect.

Compound (I) or the pharmaceutically acceptable salt thereof can be administered as they are, or in the form of various pharmaceutical compositions. The pharmaceutical compositions in accordance with the present invention can be prepared by uniformly mixing an effective amount of Compound (I) or a pharmaceutically acceptable salt thereof, as an active ingredient, with a pharmaceutically acceptable carrier. It is desired that such pharmaceutical compositions are prepared in a unit dose form suitable for oral administration or administration through injection.

For preparing a pharmaceutical composition for oral administration, any useful pharmaceutically acceptable carrier can be used. For example, liquid preparations for oral administration such as suspension and syrup can be prepared using water, sugars such as sucrose, sorbitol, and fructose, glycols such as polyethylene glycol and propylene glycol, oils such as sesame oil, olive oil, and soybean oil, preservatives such as p-hydroxybenzoates, flavors such as strawberry flavor and peppermint, and the like. Powders, pills, capsules, and tablets can be prepared using excipients such as lactose, glucose, sucrose, and mannitol, disintegrators such as starch and sodium alginate, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are the most useful oral unit dose forms because of the readiness of administration. For preparing tablets and capsules, solid pharmaceutical carriers are used.

Injectable preparations can be prepared using a carrier such as distilled water, a salt solution, a glucose solution or a mixture of a salt solution and a glucose solution. The preparations can be prepared in the form of solution, suspension, or dispersion according to a conventional method by using a suitable solubilizing agent or suspending agent.

Compound (I) or the pharmaceutically acceptable salt thereof can be administered orally in the dosage forms or parenterally as injections. The effective dose and the administration schedule vary depending upon the mode of administration, the age, body weight, and conditions of a patient, etc. However, generally, Compound (I) or a pharmaceutically acceptable salt thereof is administered in a daily dose of 1 to 50 mg/kg in 3 to 4 portions.

Certain embodiments of the invention are illustrated in the following examples, preparation examples and reference examples.

EXAMPLE 1

8-(9-Oxo-3-tricyclo[3.3.1.0$^{3,7}$]nonyl)-1,3-dipropylxanthine (Compound 1)

A suspension of Compound E (250 mg, 0.644 mmol) obtained in Reference Example 1 and calcium hydroxide (334 mg, 4.51 mmol) in 4 ml of water was heated under reflux for 30 minutes. The mixture was cooled, adjusted to pH 2 with concentrated hydrochloric acid and extracted three times with chloroform. The extracts were washed with saturated aqueous sodium chloride, and dried over anhydrous magnesium sulfate and the solvent was evaporated under reduced pressure. The residue was recrystallized from ethanol/water, to give 141 mg (yield 59%) of Compound 1 as a white plate crystal.

Melting Point: 172.0°–173.7° C. Elemental Analysis: $C_{20}H_{26}N_4O_3$ Calcd. (%): C, 64.85; H, 7.07; N, 15.12 Found (%): C, 64.43; H, 7.33; N, 15.21 IR(KBr) $v_{max}$ (cm$^{-1}$): 1703, 1650, 1560, 1501. NMR(270 MHz; CDCl$_3$) δ (ppm): 12.14(1H, brs), 4.12(2H, t, J=7.3 Hz), 3.97(2H, t, J=7.6 Hz), 3.16(1H, t, J=5.9 Hz), 2.89(2H, brs), 2.60–2.53 (2H, m), 2.34–2.23(4H, m), 1.98–1.93(2H, m), 1.90–1.60(4H, m), 0.98(3H, t, J=7.0 Hz), 0.94(3H, t, J=7.3 Hz). MS(EI)m/e(relative intensity): 370 (100,M+), 328(53), 300(46), 286(54), 258(35), 256(37), 217(41).

EXAMPLE 2

8-(6-Oxo-3-tricyclo[3.3.1.0$^{3,7}$]nonyl)-1,3-dipropylxanthine (Compound 2)

Substantially the same procedure as in Example 1 was repeated using Compound F (570 mg, 1.47 mmol) obtained in Reference Example 1 as a starting compound, instead of Compound E, to give 478 mg (yield 79%) of Compound 2 as a white powder.

Melting Point: 162.8°–164.1° C. Elemental Analysis: $C_{20}H_{26}N_4O_3$ Calcd. (%): C, 64.85; H, 7.07; N, 15.12

Found (%): C, 64.56; H, 7.28; N, 15.21 IR(KBr) $\nu$max(cm$^{-1}$): 1751, 1703, 1648, 1556, 1508, 1502. NMR(270 MHz; CDCl$_3$) δ (ppm): 12.18(1H, brs), 4.09(2H, t, J=7.2 Hz), 4.02(2H, t, J=7.8 Hz), 3.07(1H, dd, J=7.9, 1.7 Hz), 2.68–2.60(1H, m), 2.60–1.85 (9H, m), 1.80–1.60(4H, m), 0.97(6H, t, J=7.3 Hz). MS(EI)m/e(relative intensity): 370 (100,M+), 328(61), 300(51), 286(86), 258(39), 256(36), 217(13).

EXAMPLE 3

8-(Trans-9-hydroxy-3-tricyclo[3.3.1.0$^{3,7}$]nonyl)-1,3-dipropylxanthine (Compound 3) and 8-(cis-9-hydroxy-3tricyclo[3.3.1.0$^{3,7}$]nonyl)-1,3-dipropylxanthine (Compound 4)

To a solution of 70.0 mg (0.189 mmol) of Compound 1 obtained in Example 1 in 3 ml of ethanol, 9.2 mg (0.378 mmol) of lithium borohydride was added under ice-cooling, and stirred at room temperature for 1.5 hours. The resulting mixture was acidified with 1N hydrochloric acid to pH 3, and extracted three times with chloroform. The combined extracts were washed with a saturated aqueous sodium chloride, and dried over anhydrous magnesium sulfate and the solvent was evaporated under reduced pressure. The residue was purified by high performance liquid chromatography (HPLC) [column: YMC-Pack, SH-365-10, S-10 [YMC Co., Ltd.] 30mmi.d.×500 mm; eluent: 50% acetonitrile/water; flow rate: 80 ml/min] to give 26.6 mg (yield 38%) of Compound 3 and 11.5 mg (yield 16%) of Compound 4, as a white powder.

Compound 3:
Melting Point: 224.9°–225.3° C. Elemental Analysis: C$_{20}$H$_{28}$N$_4$O$_3$ Calcd. (%): C, 64.49; H, 7.58; N, 15.04 Found (%): C, 64.74; H, 7.37; N, 15.15 IR(KBr) $\nu_{max}$ (cm$^{-1}$): 1696, 1653, 1555, 1508, 1495. $^1$H-NMR(270 MHz; CD$_3$OD) δ (ppm): 4.07(2H, m), 3.95(2H, m), 3.89(1H, m), 2.62(1H, m), 2.34(2H, m), 2.17(2H, m), 2.10(2H, m), 1.98(2H, dd, J=10.9, 2.7 Hz), ca. 1.81(2H, m), 1.77(2H, m), 1.66 (2H, m), 0.95(3H, t, J=7.4 Hz), 0.94(3H, t, J=7.4 Hz). $^{13}$C-NMR(270 MHz; CD$_3$OD) δ (ppm): 161.8, 156.1, 153.0, 149.8, 108.4, 73.2, 49.5, 46.6, 46.3, 46.1, 44.9, 43.9, 39.7, 22.41, 22.36, 11.5, 11.4. MS(EI)m/e(relative intensity): 372(100,M+), 330(59), 302(27), 288(63), 258(17).

Compound 4:
Melting Point: 224.8°–225.1° C. Elemental Analysis: C$_{20}$H$_{28}$N$_4$O$_3$ Calcd. (%): C, 64.49; H, 7.58; N, 15.04 Found (%): C, 64.58; H, 8.01; N, 14.94 IR(KBr) $\nu_{max}$ (cm$^{-1}$): 1694, 1650, 1499. $^1$H-NMR(270 MHz; CD$_3$OD) δ (ppm): 4.08(2H, m), 3.95(2H, m), 3.86(1H, m), 2.68(1H, bt, J=6.6 Hz), 2.36(2H,m), ca. 2.35(2H, m), 2.01–1.90(4H, m), 1.78(2H, m), 1.66(2H, m), ca. 1.65(2H, m), 0.96(3H, t, J=7.4 Hz), 0.94(3H, t, J=7.4 Hz). $^{13}$C-NMR(270 MHz; CD$_3$OD) δ (ppm): 161.9, 156.1, 153.0, 149.8, 108.4, 72.7, 49.8, 46.1, 45.2, 45.1, 44.8, 43.9, 41.3, 22.41, 22.35, 11.5, 11.3. MS(EI)m/e(relative intensity): 372(100,M+), 330(26), 302(10), 288(44), 258(18).

EXAMPLE 4

8-(Trans-6-hydroxy-3-tricyclo[3.3.1.0$^{3,7}$]nonyl)-1,3-dipropylxanthine (Compound 5)

Substantially the same procedure as in Example 3 was repeated using 75.0 mg (0.203 mmol) of Compound 2 obtained in Example 2 as a starting compound. The obtained crude product was recrystallized from ethanol/water to give 56.8 mg (yield 75%) of Compound 5 as a white powder.

Melting Point: 192.8°–193.5° C. Elemental Analysis: C$_{20}$H$_{28}$N$_4$O$_3$ Calcd. (%): C, 64.49; H, 7.58; N, 15.04 Found (%): C, 64.78; H, 7.81; N, 15.20 IR(KBr) $\nu_{max}$ (cm$^{-1}$) 1703, 1654, 1553, 1500. $^1$H-NMR (270 MHz; CD$_3$OD) δ (ppm): 4.22(1H, dd, J=6.9, 3.3 Hz), 4.07(2H, m), 3.95(2H, m), 2.59(1H, tt, J=6.9, 1.3 Hz), 2.51(1H, dd, J=11.4, 2.1 Hz), 2.30(1H,m), ca. 2.18(2H, m), 2.10(1H, m), ca. 2.02(1H, m), ca. 1.97(1H, m), 1.91(1H, d, J=11.5 Hz), 1.78(2H, m), 1.66(2H, m), ca. 1.55(1H, m), ca. 1.48(1H, m), 0.95(3H, t, J=7.4 Hz), 0.94(3H, t, J=7.4 Hz). $^{13}$C-NMR (270 MHz; CD$_3$OD) δ (ppm): 161.9, 156.1, 153.0, 149.8, 108.4, 76.5, 49.4, 49.3, 46.1, 43.9, 43.7, 41.9, 38.2, 34.1, 30.4, 22.4, 22.3, 11.5, 11.3. MS(EI)m/e(relative intensity): 372(100,m+), 370(81), 354(44), 330(50), 328(54), 288(81), 286(64).

EXAMPLE 5

8-(Trans-9-hydroxy-3-tricyclo[3.3.1.0$^{3,7}$]nonyl)-1,3-dipropylxanthine (Compound 3)

1) Preparation of rat hepatocyte microsome

Phenobarbital Sodium (product of Wako Pure Chemical Industries, Ltd.) was intraperitoneally administered to male rats (SD strain, SLC, 200–220 g) at a dose of 80 mg/kg, once a day for 3 days. The liver was taken out of the rat on the fourth day, and suspended in ice-cooled 1.15% potassium chloride-0.01M phosphate buffer (pH 7.4), having the 3-fold volume of the weight of the liver, with Teflon homogenizer. The suspension was centrifuged (10,000×g, 10 minutes, 4° C.) and the supernatant was further centrifuged (105,000×g, 60 minutes, 4° C.). The precipitate was suspended again in the same amount of 1.15% potassium chloride-0.01M phosphate buffer (pH 7.4), and centrifuged (40,000×g, 30 minutes, 4° C.). The precipitate thus obtained was suspended in 20% glycerol and 0.1 mM disodium ethylenediamine tetraacetate (EDTA)-0.01M phosphate buffer (pH 7.4) to a final concentration of 10 mg (wet weight)/ml to give rat hepatocyte microsome.

2) Synthesis of Compound 3 by use of the rat hepatocyte microsome 3.6 mg (0.01 mmol) of 8- (3-noradamantyl) -1,3-dipropylxanthine[1,3-dipropyl-8-(3-tricyclo[3.3.1.0$^{3,7}$-]nonyl)xanthine (as described in Japanese Published Unexamined Patent Application No. 173889/91) was dissolved in 1 ml of methanol, and 10 ml of the previously obtained rat hepatocyte microsome, 5 ml of 4% bovine serum albumin (BSA)/0.2M phosphate buffer (pH 7.4), 2 ml of NADPH-generating reaction mixture [8 mM sodium β-nicotinamide adenine dinucleotide phosphate (β-NADP), 80 mM sodium glucose-6-phosphate, 10 units of glucose 6-phosphate dehydrogenase (derived from yeast: Oriental Yeast Co., Ltd.) and 60 mM magnesium chloride] and 2 ml of 1 mM EDTA were added, and the mixture was incubated at 37° C. for 1 hour. The reaction mixture was centrifuged (40,000×g, 30 minutes, 4° C.), and the supernatant was collected, and the precipitate was suspended once again in 0.2M phosphate buffer. To the suspension, 5 ml of 4% bovine serum albumin (BSA)/0.2M phosphate buffer (pH 7.4), 2 ml of an NADPH-generating reaction mixture [8 mM β-NADP, 80 mM glucose-6-phosphate, 10 units of glucose 6-phosphate dehydrogenase (derived from yeast: Oriental Yeast Co., Ltd.) and 60 mM magnesium chloride] and 2 ml of 1 mM EDTA were added once again and centrifuged again (40,000×g, 30 minutes, 4° C.) and the supernatant was obtained. The procedure was repeated further four times, and all the supernatants were combined, and 600 μl of an aqueous 2N sodium hydroxide and 20 ml of ethyl acetate were added, and the mixture was shaken and stirred. The organic layer was separated by centrifugation (2500 rpm×5 minutes) and concentrated. The residue was purified by HPLC [column:YMC AM-312(ODS) 5 μm [YMC Co., Ltd.] 6 mmi.d.×150 mm; eluent: 40% acetonitrile/an aqueous 50 mM ammonium acetate; flow rate: 1 ml/min], to give ca. 400 μg (yield ca. 10%) of Compound 3 as a white powder.

EXAMPLE 6

3-(3-Hydroxypropyl)-8-(3-tricyclo[3.3.1.0$^{3,7}$]nonyl)-1-propylxanthine (Compound 6) and 3-(2-hydroxypropyl) -8-(3tricyclo[3.3.1.0$^{3,7}$]nonyl)-1-propylxanthine (Compound 7)

100 mg (0.282 mmol) of Compound H obtained in Reference Example 2 was dissolved in 1 ml of tetrahydrofuran. To the solution was added dropwise diborane-dimethylsulfide complex (10M tetrahydrofuran solution, 28 μl, 0.28 mmol), and the resulting mixture was stirred at room temperature for 1 hour. After cooling to 0° C., 1 ml of ethanol, 330 μl of aqueous 2N sodium hydroxide, 250 μl of aqueous 35% hydroperoxide were added and the resulting mixture was again stirred at room temperature for 1 hour. The reaction mixture was neutralized and extracted three times with chloroform. The organic layer was dried over anhydrous magnesium sulfate, and the solvent was evaporated under reduced pressure to give 106 mg of a ca. 6:4 mixture (quantitatively) of Compound 6 and Compound 7 as a white powder.

The mixture was purified by HPLC [column:YMC Pack D-ODS-5[YMC Co., Ltd.] 250 mm×20 mm; eluent: 50% acetonitrile/water; flow rate:13 ml/min.] to give 31.9 mg of Compound 6 and 21.4 mg of Compound 7, as a white powder.

Compound 6:

Melting Point: 155.0°-156.0° C. (recrystallized from ethanol/water) Elemental Analysis: $C_{20}H_{28}N_4O_3$ Calcd. (%): C, 64.49; H, 7.58; N, 15.04 Found (%): C, 64.56; H, 7.76; N, 14.73 IR(KBr) $\nu_{max}$(c$^{-1}$): 3400, 3180, 1700, 1653, 1506. NMR(270 MHz; CDCl$_3$) δ (ppm): 11.79(1H, brs), 4.31(2H, t, J=5.4 Hz), 4.00(2H, t, J=7.4 Hz), 3.49(2H, t, J=5.4 Hz), 2.78(1H, t, J=6.4 Hz), 2.50-2.40(2H, m), 2.30-2.20(2H,m), 2.15-1.70(13H, m), 0.96(3H, t, J=7.4 Hz).

Compound 7:

Melting Point: 220.0°-222.0° C. (recrystallized from methanol) Elemental Analysis: $C_{20}H_{28}N_4O_3$ Calcd. (%): C, 64.49; H, 7.58; N, 15.04 Found (%): C, 63.97; H, 7.81; N, 14.75 IR(KBr) $\nu_{max}$ (c$^{-1}$): 3470, 3180, 1701, 1632, 1500. NMR(270 MHz; CDCl$_3$) δ ( ppm): 4.50-4.40(1H, m), 4.35-4.15(2H, m), 4.00(2H, t, J=7.4 Hz), 2.78(1 H, t, J=6.5 Hz), 2.45-1.50(15H, m), 1.28(3H, d, J=6.0 Hz), 0.96(3H, t, J=7.4 Hz)

EXAMPLE 7

8-(3-Hydroxy-1-tricyclo[3.3.1.1$^{3,7}$]decyl)-1,3-dipropylxanthine (Compound 8)

To a solution of 1.10 g (5.61 mmol) of 3-hydroxy-1-adamantane carboxylic acid (3-hydroxy-1-tricyclo [3.3.1.1$^{3,7}$]decane carboxylic acid) [Syn. Commun. 18, 1967 (1988)] in a mixture of 10 ml-methylene chloride and 25 ml-dimethyl formamide, 1.03 g (6.73 mmol) of 1-hydroxy benzotriazole and 1.61 g (8.42 mmol) of 1-(3-dimethylaminopropyl)-3-ethylcarbodiimide were added and stirred at room temperature for 30 minutes. To the reaction mixture was added dropwise 15 ml of a solution of 5,6-diamino-1,3-dipropyluracil in methylene chloride under ice-cooling and with stirring, and the resulting mixture was stirred at room temperature for 1 hour. 50 ml of a saturated aqueous sodium bicarbonate was added to the resulting mixture and extracted three times with chloroform. The combined organic layer was washed with a saturated aqueous sodium chloride twice and dried over anhydrous magnesium sulfate and the solvent was evaporated under reduced pressure. A suspension of the obtained residue and calcium hydroxide (2.77 g, 37 mmol) in 35 ml of water was heated under reflux for 3 hours. The mixture was then cooled, adjusted to pH 2 with concentrated hydrochloric acid, and extracted three times with chloroform. The extracts were washed with a saturated aqueous sodium chloride, dried over anhydrous magnesium sulfate and the solvent was evaporated under reduced pressure. The residue was purified by silica gel column chromatography (eluent: 4% methanol/chloroform), and recrystallized from hexane/toluene to give 680 mg (yield 33%) of Compound 8 as a white plate crystal.

Melting Point: 213.1°-214.3° C. Elemental Analysis: $C_{21}H_{30}N_4O_3$ Calcd. (%): C, 65.26; H, 7.82; N, 14.50 Found (%): C, 65.13; H, 8.08; N, 14.54 IR(KBr) $\nu_{max}$ (c$^{-1}$): 3510, 3148, 2906, 1703, 1637, 1544, 1494. NMR(270 MHz; DMSO-d$_6$) δ (ppm): 12.96(1H, brs), 4.56(1H, s), 3.94(2H, t, J=7.5 Hz), 3.83(2H, t, J=7.3 Hz), 2.19(2H, brs), 1.90-1.48(16H,m), 0.86(3H, t, J=7.4 Hz), 0.85(3H, t, J=7.4 Hz).

EXAMPLE 8

1-(2-Oxopropyl)-8-(3-tricyclo[3.3.1.0$^{3,7}$]nonyl)-3-propylxanthine (Compound 9)

Substantially the same procedure as in Example 1 was repeated using 1.70 g (4.38 mmol) of Compound I obtained in Reference Example 3 as a starting compound. The obtained crude product was recrystallized from acetone/water to give 874 mg (yield 54%) of Compound 9 as a white plate crystal.

Melting Point: 210.8°-212.5° C. Elemental Analysis: $C_{20}H_{26}N_4O_3$ Calcd. (%): C, 64.85; H, 7.07; N, 15.12 Found (%): C, 65.21; H, 7.47; N, 15.19 IR(KBr) $\nu_{max}$ (cm$^{-1}$): 1720(sh), 1700, 1655, 1553, 1499. $^1$H-NMR(270 MHz; CDCl$_3$) δ (ppm): 4.83(2H, s), 4.09(2H, t, J=7.5 Hz), 2.74(1H, t, J=6.9 Hz), 2.39(2H, brs), 2.25(3H, s), 2.27-2.20(2H, m), 1.95-1.60(10H, m), 0.96(3H, t, J=7.4 Hz). MS(EI)m/e(rel intensity): 370(M+, 100), 327(86).

EXAMPLE 9

1-(2-Hydroxypropyl)-8-(3-tricyclo[3.3.1.0$^{3,7}$]nonyl)-3-propylxanthine (Compound 10)

Substantially the same procedure as in Example 3 was repeated using 780 mg (2.11 mmol) of Compound 9 obtained in Example 8. The obtained crude product was recrystallized from acetonitrile to give 440 mg (yield 56%) of Compound 10 as a white prismatic crystal.

Melting Point: 194.7°-196.9° C. Elemental Analysis: $C_{20}H_{28}N_4O_3$ Calcd. (%): C, 64.49; H, 7.58; N, 15.04 Found (%): C, 64.59; H, 7.84; N, 15.07 IR(KBr) $\nu_{max}$ (c$^{-1}$):1703, 1655, 1553, 1497. $^1$H-NMR(270 MHZ; CDCl$_3$) δ (ppm): 10.84(1H, brs), 4.17-4.06(5H, m), 3.23

(1H, d, J=4.9 Hz), 2.76(1H, t, J=6.9 Hz), 2.41(2H, brs), 2.22–2.18(2H, m), 2.05–1.68(10H, m), 1.26(3H, d, J=5.6 Hz ), 0.97(3H, t, J=7.4 Hz). $^{13}$C-NMR(270 MHz; CD$_3$OD) δ (ppm): 162.4, 156.2, 153.3, 149.8, 108.2, 66.6, 50.7, 49.8, 48.9, 46.9, 46.0, 44.7, 39.0, 35.7, 22.4, 21.1, 11.4. MS(EI)m/e(rel. intensity): 372(M+, 12), 354(21), 328(19), 315(100), 279(22).

EXAMPLE 10

1-(3-Oxopropyl)-8-(3-tricyclo[3.3.1.0$^{3,7}$]nonyl)-3-propylxanthine (Compound 11)

A solution of 35.0 mg (0.10 mmol) of Compound J obtained in Reference Example 4 in 3 ml of N,N-dimethylformamide was added dropwise to a mixture of 0.5 ml-N,N-dimethylformamide and 0.5 ml-water containing 3.6 mg (0.02 mmol) of palladium chloride and 2.7 mg (0.02 mmol) of cupric chloride. The reaction mixture was stirred at 50° C. for 2 hours in an oxygen atmosphere, poured into 20 ml of ice water, extracted three times with chloroform. The extracts were washed with water, and with a saturated aqueous sodium chloride, and dried over anhydrous magnesium sulfate. The solvent was evaporated under reduced pressure, and the residue was purified by silica gel column chromatography to give 10.4 mg (yield 28%) of 1-(2-oxopropyl)-8-(3-tricyclo[3.3.1.0$^{3,7}$]nonyl)-3-propylxanthine (Compound 9) and 9.9 mg (yield 27%) of Compound 11, as a white powder.

Compound 11:

Melting Point: 180.9°–183.8° C. IR(KBr) $v_{max}$($^{cm-1}$): 1728(sh), 1699, 1657, 1554, 1495. $^1$H-NMR(270 MHz; CDCl$_3$) δ (ppm): 11.40(1H, brs), 9.83(1H, s), 4.40(2H, t, J=7.0 Hz), 4.09(2H, t, J=7.4 Hz), 2.86–2.72(3H, m), 2.41(2H, brs), 2.22–2.18(2H, m), 2.05–1.65(12H, m), 0.97(3H, t, J=7.4 Hz). MS(EI)m/e: 370(M+).

EXAMPLE 11

8-(Trans-9-hydroxy-3-tricyclo[3.3.1.0$^{3,7}$]nonyl)-1-(2-oxopropyl)-3-propylxanthine (Compound 12), 8-(cis-9-hydroxy-3-tricyclo[3.3.1.0$^{3,7}$]nonyl) -1-(2-oxopropyl)-3-propylxanthine (Compound 14) and 8-(trans-6-hydroxy-3-tricyclo[3.3.1.0$^{3,7}$]nonyl)-1-(2-oxopropyl)-3-propylxanthine (Compound 16)

Substantially the same procedure as in Example 1 was repeated using 208 mg (0.515 mmol) of a 1:1:8 mixture of Compound P, Compound Q and Compound R as obtained in Reference Example 5. The obtained crude product was purified by HPLC [Column: YMC-Pack, SH-365-10, S-10 [YMC Co., Ltd. ] 30 mmi.d.×500 mm; eluent: 25% acetonitrile/water; flow rate: 40 ml/min] to give 12.9 mg (yield: 6.5%) of Compound 12, 9.3 mg (yield: 4.7%) of Compound 14 and 90.4 mg (yield: 46%) of Compound 16, as a white powder.

Compound 12:

Melting point: 254.8°–256.8° C. IR(KBr) $v_{max}$ (cm$^{-1}$):1720(sh), 1703, 1655, 1499. $^1$H-NMR(270 MHz; CD$_3$OD) δ (ppm): 4.84(2H, s), 4.07(2H, t, J=7.4 Hz), 3.89(1H, m), 2.63(1H, t, J=7.0 Hz), 2.33(2H, m), 2.24(3H, s), 2.17(2H, m), 2.10(2H, m), 1.99(2H, dd, J=10.9, 2.8 Hz ), 1.85–1.70(4H, m), 0.95(3H, t, J=7.4 Hz). MS(EI) m/e: 386 (M+).

Compound 14

Melting point: 238.1°–241.8° C. IR(KBr) $v_{max}$ (cm$^{-1}$): 1718(sh), 1705, 1650, 1494. $^1$H-NMR(270 MHz; CD$_3$OD) δ (ppm): 4.83(2H, s), 4.07(2H, t, J=7.4 Hz), 3.86(1H, m), 2.68(1H, t, J=6.4 Hz), 2.36(2H, m), 2.35(2H, m), 2.23(3H, s), 2.01–1.90(4H, m), 1.77(2H, m), 1.65(2H, dd, J=11.3, 2.9 Hz), 0.95(3H, t, J=7.4 Hz). MS(EI) m/e: 386 (M+).

Compound 16:

Melting point: 214.6°–215.7° C. IR(KBr) $v_{max}$ (cm$^{-1}$): 1720(sh), 1703, 1650, 1498. $^1$H-NMR(270 MHz; CD$_3$OD) δ (ppm): 4.84(2H, s), 4.22(1H, dd, J=6.9, 3.0 Hz), 4.07(2H, t, J=7.4 Hz), 2.60(1H, t, J=6.7 Hz), 2.51(1H, dd, J=11.3, 2.0 Hz), 2.29(1H, m), 2.23(3H, s), 2.20(2H, m), 2.10(1H, m), 2.05–1.95(2H, m), 1.90(1H, d, J=11.9 Hz), 1.77(2H, m), 1.60–1.52(1H, m), 1.48(1H, m), 0.95(3H, t, J=7.4 Hz). MS(EI) m/e: 386 (M+).

EXAMPLE 12

1-(2-Hydroxypropyl)-8-(trans-9-hydroxy-3-tricyclo[3.3.1.0$^{3,7}$]nonyl)-3-propylxanthine (Compound 13)

Substantially the same procedure as in Example 3 was repeated using 8.4 mg (0.0218 mmol) of Compound 12 as obtained in Example 11 and 1.0 mg (0.0265 mmol) of sodium borohydride to give 7.4 mg (yield 88%) of Compound 13 as a white powder.

Melting point: 210.2°–214.8° C. IR(KBr) $v_{max}$ (c$^{-1}$): 1701, 1642, 1495. $^1$H-NMR(270 MHz; CD$_3$OD) δ (ppm): 4.15–4.05(2H, m), 4.07(2H, t, J=7.4 Hz), 3.95–3.86(1H, m), 3.88(1H, m), 2.61(1H, t, J=6.5 Hz), 2.33(2H, m), 2.17(2H, m), 2.10 (2H, m), 1.97(2H, dd, J=10.4, 2.6 Hz), 1.85–1.70(4H, m), 1.18(3H, d, J=7.0 Hz), 0.95(3H, t, J=7.4 Hz). MS(EI) m/e: 388 (M+).

EXAMPLE 13

1-(2-Hydroxypropyl)-8-(cis-9-hydroxy-3-tricyclo[3.3.1.0$^{3,7}$]nonyl)-3-propylxanthine (Compound 15)

Substantially the same procedure as in Example 3 was repeated using 6.4 mg (0.0167 mmol) of Compound 14 as obtained in Example 11 and 1.0 mg (0.0265 mmol) of sodium borohydride to give 5.2 mg (yield: 80%) of Compound 15 as white powder.

Melting point: 221.8°–222.6° C. IR(KBr) $v_{max}$ (c$^{-1}$): 1706, 1645, 1500. $^1$H-NMR(270 MHz; CD$_3$OD) δ (ppm): 4.15–4.05(2H, m), 4.07(2H, t, J=7.4 Hz), 3.94–3.85(1H, m), 3.86(1H, m), 2.67(1H, t, J=6.4 Hz), 2.35(2H, m), 2.34(2H, m), 2.01–1.90(4H, m), 1.77(2H, m), 1.65(2H, dd, J=11.4, 3.0 Hz), 1.18(3H, d, J=6.9 Hz), 0.96(3H, t, J=7.4 Hz). MS(EI) m/e: 388 (M+).

EXAMPLE 14

1-(2-Hydroxypropyl)-8-(trans-6-hydroxy-3-tricyclo[3.3.1.0$^{3,7}$]nonyl)-3-propylxanthine (Compound 17)

Substantially the same procedure as in Example 3 was repeated using 57.4 mg (0.149 mmol) of Compound 16 as obtained in Example 11 and 6.1 mg (0.161 mmol) of sodium borohydride to give 48.6 mg (yield: 84%) of Compound 17 as a white powder.

Melting point: 200.1°–201.0° C. IR(KBr) $v_{max}$ (c$^{-1}$): 1699, 1647, 1498. $^1$H-NMR(270 MHz; CD$_3$OD) δ (ppm): 4.22(1H, dd, J=6.9, 3.3 Hz), 4.15–4.05(2H, m), 4.07(2H, t, J=7.4 Hz), 3.89(1H, m), 2.58(1H, t, J=6.9 Hz), 2.51(1H, dd, J=11.3, 2.0 Hz), 2.30(1H, m), 2.20(2H, m), 2.10(1H, m), 2.05–1.95(2H, m), 1.91(1H, d, J=11.4 Hz), 1.77(2H, m), 1.60–1.52(1H, m), 1.48(1H, m), 1.18(3H, d, J=7.0 Hz), 0.95(3H, t, J=7.4 Hz). MS(EI) m/e: 388 (M+).

Preparation Example 1

Tablet

Tablets comprising the following composition were prepared by a conventional method.

40 g of Compound 1, 286.8 g of lactose, and 60 g of potato starch were mixed and 120 g of aqueous 10% hydroxypropylcellulose was added thereto. The resulting mixture was mixed, granulated and dried. The particle size was controlled. 1.2 g of magnesium stearate was added and mixed with the resulting granules and tablets (each tablet contains 20 mg of an active ingredient) were produced by tablet making machine having a striker of 8 mm diameter (RT-15 type manufactured by Kikusuisha).

| Formulation: | Compound 1 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Preparation Example 2

Granule

Granules comprising the following composition were prepared by a conventional method.

20 g of Compound 3, 655 g of lactose and 285 g of corn starch were mixed and 400 g of 10% aqueous hydroxypropyl-cellulose solution was added. The resulting mixture was mixed, granulated and dried, to provide granules. 20 mg of an active ingredient was contained per 1,000 mg of the granules.

| Formulation: | Compound 3 | 20 mg |
|---|---|---|
| | Lactose | 655 mg |
| | Corn starch | 285 mg |
| | Hydroxypropylcellulose | 40 mg |
| | | 1,000 mg |

Preparation Example 3

Capsule

Capsules comprising the following composition were prepared by a conventional method.

200 g of Compound 6, 995 g of AVICEL and 5 g of magnesium stearate were mixed by a conventional method. The resulting mixture was filled in a hard capsule No. 4 (with the volume of 120 mg per 1 capsule) by capsule charger (LZ-64 type manufactured by Zanashi Co.) to provide capsules. 50 mg of an active ingredient was contained per 1 capsule.

| Formulation: | Compound 6 | 20 mg |
|---|---|---|
| | AVICEL | 99.5 mg |
| | Magnesium stearate | 0.5 mg |
| | | 120 mg |

Preparation Example 4

Injection

Injection comprising the following composition was prepared by a conventional method.

1 g of Compound 7 was dissolved in 100 g of refined soybean oil, and 12 g of refined egg yolk lecithin and 25 g of glycerin for injection were added. Injectable distilled water was added to make the total volume 1000 ml and the resulting mixture was mixed and emulsified by a conventional method. The resulting dispersion was filtered (sterile filtration) through a 0.2 μm disposable membrane filter, then injected in a glass vial under sterilized condition by 2 ml. The injection contained 2 mg of an active ingredient per 1 vial.

| Formulation: | Compound 7 | 2 mg |
|---|---|---|
| | Refined soybean oil | 200 mg |
| | Refined egg yolk lecithin | 24 mg |
| | Glycerin for injection | 50 mg |
| | Distilled water for injection | 1.72 ml |
| | | 2.00 ml |

Reference Example 1

6-Amino-5-(9-oxo-3-tricyclo[3.3.1.0$^{3,7}$]nonylcarbonylamino)-1,3-dipropyluracil (Compound E) and 6-amino-5-(6-oxo-3-tricyclo[3.3.1.0$^{3,7}$]nonylcarbonylamino)-1,3-dipropyluracil (Compound F)

To a solution of 6.95 g (38.6mmol) of tricyclo[3.3.1.0$^{3,7}$]nonane-3-carboxylic acid methyl ester in 175 ml of anhydrous acetic acid and 70 ml of glacial acetic acid, 23.1 g (231 mmol) of chromic anhydride in 35 ml-water was added under ice-cooling over a one-hour period (the inside temperature: 10°–15° C.) and stirred at room temperature for 3 days. The resulting mixture was poured into 3 of ice-water and extracted three times with 200 ml portions of ether. The combined organic layer was washed with water, with a saturated sodium chloride aqueous solution, and dried over anhydrous magnesium sulfate. The solvent was evaporated under reduced pressure. The residue was purified by silica gel column chromatography to give 1.64 g (yield 22%) of a ca. 1:2 mixture of 9-oxotricyclo[3.3.1.0$^{3,7}$]nonane-3-carboxylic acid methyl ester (Compound A) and 6-oxotricyclo[3.3.1.0$^{3,7}$]nonane-3-carboxylic acid methyl ester (Compound B) as a pale yellow oily substance.

NMR(270 MHz; CDCl$_3$) δ (ppm): 3.76(3×1/3H, s, CO$_2$CH$_3$ of A), 3.72(3×2/3H, s, CO$_2$CH$_3$ of B), 2.98(1×1/3H, t, J=6.3 Hz, C7—H of A), 2.81–2.79(1×/3H, m, C7—H of B), 2.79–2.76 (2×1/3H, m, C1—H and C5—H of A), 2.55–2.45(2×2/3H, m, C1—H and C5—H of B), 2.35–1.82(8H, m). $^{13}$C-NMR(270 MHz; CDCl$_3$) δ (ppm): 215.2(C=O of B), 212.2(C=O of A), 175.9(C*O$_2$CH$_3$ of A), 175.3(C=O$_2$CH$_3$ of B), 52.7(C3 of A), 52.1(C1 and C5 of A), 52.1 (CO$_2$C*H$_3$ of A), 52.0(CO$_2$C*H$_3$ of B), 51.9(C7 of B), 50.3(C3 of B), 48.0(C5 of B), 46.6(C2 and C4 of A), 46.0(C4 of B), 45.2(C2 of B), 43.5(C6 and C8 of A), 42.7(C7 of A), 39.4(C8 of B), 37.0(C9 of B), 36.3(C1 of B).

To a solution of 1.04 g ( 8.45 mmol ) of a ca. 1:2 mixture of Compound A and Compound B as obtained above in 30 ml of methanol, 1.42 g(33.8 mmol) of lithium hydroxide in 15 ml of water was added to the solution. The mixture was stirred at room temperature for 2 hours. The resulting mixture was adjusted to pH 3 with concentrated hydrochloric acid, and extracted 4 times with 20 ml portions of ether. The combined extracts were washed with a saturated aqueous sodium chloride solution, and dried over anhydrous magnesium sulfate. The solvent was evaporated under reduced pressure to give 1.38 g (yield 90%) of a ca. 1:2 mixture of 9-oxotricyclo [3.3.1.0$^{3,7}$]nonane-3-carboxylic acid (Compound C) and 6-oxotricyclo [3.3.1.0$^{3,7}$]nonane-3-carboxylic acid (Compound D) as a colorless crystalline powder.

NMR(270 MHz; CDCl₃) δ (ppm): 3.04(1×1/3H, t, J=6.0 Hz), 2.84–2.81(1×2/3H, m), 2.80–2.76(2×1/3H, m), 2.60–2.45(2×2/3H, m), 2.35–1.75(8H, m).

To a solution of 1.00 g (5.56 mmol) of a ca. 1:2 mixture of Compound C and Compound D as obtained above in a mixture of 10 ml of methylene chloride and 25 ml of dimethyl formamide, 1.07 g (7.00 mmol) of 1-hydroxybenzotriazole and 1.10 g (8.34 mmol) of 1-(3-dimethylaminopropyl)-3-ethylcarbodiimide were added and the mixture was stirred at room temperature for 30 minutes. 1.20 g (5.29 mmol) of 5,6-diamino-1,3-dipropyluracil in 15 ml of methylene chloride was added dropwise to the reaction mixture with stirring under ice-cooling, and the resulting mixture was stirred at room temperature for one hour. 50 ml of a saturated aqueous sodium bicarbonate solution was added to the resulting mixture, and extracted three times with chloroform. The combined organic layer was washed twice with a saturated aqueous sodium chloride solution, dried over anhydrous magnesium sulfate, and the solvent was evaporated under reduced pressure. The residue was purified by HPLC (column:YMC-Pack, SH-365-10, S-10 [YMC Co., Ltd.] 30 mmi.d.×500 mm; eluent: 27.5% acetonitrile/10 mM ammonium acetate aqueous solution; flow rate: 80 ml/min] to give 298 mg (yield 15%) of Compound E and 655 mg (yield 32%) of Compound F, as a white powder.

Compound E:

Melting Point: 125.6°–127.1° C. IR(KBr) $v_{max}$ (c$^{-1}$): 3350(br), 1700, 1656, 1593, 1494. NMR(270 MHz; CDCl₃) δ (ppm): 7.51(1H, brs), 5.54(2H, brs), 3.93–3.86(4H, m), 3.10(1H, t, J=6.2 Hz), 2.84(2H, brs), 2.39–2.32(2H, m), 2.21–2.13(4H, m), 1.93–1.88(2H, m), 1.85–1.60(4H, m), 1.02(3H, t, J=7.3 Hz), 0.94(3H, t, J=7.2 Hz). MS(EI) m/e (relative intensity): 388(63, M+), 225(100), 163(17). MS(HR)m/e: Calcd. (C₂₀H₂₈N₄O₄) 388.2111; Found 388.2126

Compound F:

Melting Point: 179.7°–181.2° C. IR(KBr) $v_{max}$ (cm$^{-1}$): 3320(br), 1741, 1699, 1619, 1509. NMR(270 MHz; CDCl₃) δ (ppm): 7.41(1H, brs), 5.50(2H, brs), 3.92–3.85(4H, m), 2.92(1H, dd, J=8.0, 1.8 Hz), 2.61(1H, brs), 2.54(1H, brs), 2.44–1.55(12H, m), 1.01(3H, t, J=7.4 Hz), 0.93(3H, t, J=7.4 Hz). MS(EI)m/e(relative intensity): 388(43, M+), 370(16), 225(100), 183(18). MS(HR)m/e: Calcd. (C₂₀H₂₈N₄O₄) 388.2111; Found 388.2119

Reference Example 2

3-Allyl-1-propyl-8-(3-tricyclo[3.3.1.0³,⁷]nonyl)xanthine (Compound H)

To a solution of 3.22 g (19.4 mmol) of tricyclo[3.3.1.0³,⁷]nonane-3-carboxylic acid in 80 ml of pyridine, 1.54 ml (21.1 mmol) of thionyl chloride was added dropwise under ice-cooling, and the mixture was stirred at room temperature for 50 minutes. 3.21 g (17.6 mmol) of 1-allyl-5,6-diaminouracil (U.S. Pat. No.2,673,848) was added slowly under ice-cooing and the mixture was stirred at room temperature for 2 hours. The reaction mixture was concentrated under reduced pressure, and extracted 5 times with chloroform/methanol (5:1). The combined organic layer was dried over anhydrous sodium sulfate, and the solvent was evaporated under reduced pressure. 30 ml of dioxane and 60 ml of 1N sodium hydroxide aqueous solution were added to the residue, and the mixture was heated under reflux for 30 minutes. The reaction mixture was cooled, neutralized and extracted three times with chloroform. The combined organic layer was dried over anhydrous sodium sulfate, and the solvent was evaporated under reduced pressure to give 4.92 g (yield 90%) of 3-allyl-8-(3-tricyclo[3.3.1.0³,⁷]nonyl)xanthine (Compound G) as a pale yellow plate crystal.

Melting Point: >270° C. (recrystallized from ethanol/water) Elemental Analysis: C₁₇H₂₀N₄O₂ Calcd. (%): C, 65.36; H, 6.45; N, 17.93 Found (%): C, 64.98; H, 6.72; N, 17.86 IR(KBr) $v_{max}$(c$^{-1}$): 1685, 1648, 1643, 1498, 1425. NMR(90 MHz; CDCl₃) δ (ppm): 12.10(1H, brs), 7.20(1H, s), 6.20–5.65(1H, m), 5.45–5.05(2H, m), 4.80–4.45(2H, m), 2.71(1H, t), 2.55–1.50(12H, m).

1.00 g (3.21 mmol) of Compound G was dissolved in 30 ml of dimethylformamide, and 256 mg of sodium hydride (60%, 6.41 mmol) was added slowly to the solution at 0° C. After 30 minutes, 0.33 ml (3.4 mmol) of 1-iodopropane was added dropwise slowly at the same temperature and stirred at room temperature overnight. The resulting reaction mixture was poured into 300 ml of water, neutralized and extracted three times with 100 ml of chloroform. The organic layer was washed with a saturated aqueous sodium chloride, and dried over anhydrous magnesium sulfate. The solvent was evaporated under reduced pressure. The residue was purified by silica gel column chromatography (eluate: 30% ethyl acetate/hexane) to give 225 mg (yield 20%) of Compound H as a colorless needle crystal.

Melting Point: 196.2°–197.1° C. (recrystallized from ethanol/water) Elemental Analysis: C₂₀H₂₆N₄O₂ Calcd. (%): C, 67.77; H, 7.39; N, 15.80 Found (%): C, 67.92; H, 7.66; N, 15.45 IR(KBr) $v_{max}$ (cm$^{-1}$): 1704, 1646, 1499. NMR(270 MHz; CDCl₃) δ (ppm): 6.15–5.90(1H, m), 5.40–5.20(2H, m), 4.75(2H, d, J=6.0 Hz), 4.00(2H, t, J=7.4 Hz), 2.80(1H, t, J=6.5 Hz), 2.45–2.35(2H, m), 2.30–2.20(2H, m), 2.10–1.85(4H, m), 1.75–1.55(6H, m), 0.95(3H, t, J=7.4 Hz).

Reference Example 3

6-Amino-3-(2-oxopropyl)-5-(3-tricyclo[3.3.1.0³,⁷-]nonylcarbonylamino)-1-propyluracil (Compound I)

To a solution of 2.20 g (6.63 mmol) of 6-amino-5-(3-tricyclo[3.3.1.0³,⁷]nonylcarbonylamino)-1-propyluracil (Japanese Published Unexamined Patent Application No. 173889/91) in 35 ml of dimethylformamide, 3.24 g (9.95 mmol) of cesium carbonate, 1.23 ml (13.3 mmol) of bromoacetone were added with stirring. The reaction mixture was stirred at 60° C. for 3.5 hours. The mixture was cooled, poured into 100 ml of water and extracted three times with 30 ml of chloroform. The organic layer was washed with 0.2M sodium thiosulfate aqueous solution, with water, with a saturated aqueous sodium chloride solution, and dried over anhydrous sodium sulfate. The solvent was evaporated under reduced pressure. The residue was purified by silica gel column chromatography (eluate: 2% methanol/chloroform) to give 1.70 g (yield 66%) of Compound I as a pale yellow powder.

IR(KBr) $v_{max}$ (c$^{-1}$): 1725(sh), 1701, 1637, 1491. ¹H-NMR(270 MHz; CDCl₃) δ (ppm): 7.28(1H, brs), 5.68(2H, brs), 4.74(2H, s), 3.88(2H, t, J=7.4 Hz), 2.74(1H, t, J=7.0 Hz), 2.37(2H, brs), 2.23(3H, s), 2.12–2.08(2H, m), 1.92–1.55(10H, m), 1.00(3H, t, J=7.4 Hz). MS(EI) m/e(rel. intensity): 388(M+, 70), 149(100), 121(90).

Reference Example 4

1-Allyl-8-(3-tricyclo[3.3.1.0³,⁷]nonyl) -3-propylxanthine (Compound J)

Substantially the same procedure as in Reference Example 3 was repeated using 300 mg (0.90 mmol) of 6-amino-5-(3-tricyclo[3.3.1.0³,⁷]nonylcarbonylamino)-1-propyluracil (Japanese Published Unexamined Patent Application No. 173889/91) and 0.16 ml (1.81 mmol) of allyl bromide. The obtained crude product was subjected to the same cyclization reaction that was used in Example 1, without purification, to give 110 mg (yield 35%) of Compound J as a white powder.

Melting Point: 190.8°–191.5° C. IR(KBr) $\nu_{max}$ (cm⁻¹): 1703, 1651, 1553, 1550. ¹H-NMR(270 MHz; CDCl₃) δ (ppm): 11.5(1H, brs), 5.98–5.84(1H, m), 5.22–5.13(2H, m), 4.67–4.65(2H, m), 4.12(2H, t,J=7.4 Hz), 2.78(1H, t, J=6.9 Hz), 2.40(2H, brs), 2.27–2.23(2H, m), 2.06–1.64(10H, m), 0.97(3H, t, J=7.4 Hz). MS(EI) m/e: 354(M+).

Reference Example 5

6-Amino-5-(trans-9-hydroxy-3-tricyclo[3.3.1.0³,⁷-]monylcarbonylamino)-3-(2-oxopropyl)-1-propyluracil (Compound P)

6-Amino-5-(cis-9-hydroxy-3-tricyclo[3.3.1.0³,⁷]nonylcarbonylamino)- 3-(2-oxopropyl)-1-propyluracil (Compound Q)

6-Amino-5-(trans-6-hydroxy-3-tricyclo[3.3.1.0³,⁷]nonylcarbonylamino)-3-(2-oxopropyl)-1-propyluracil (Compound R)

Substantially the same procedure as in Reference Example 1 was repeated using a 613 mg (3.40 mmol) of a ca. 1:4 mixture of Compound C and Compound D obtained in Reference Example 1, and 597 mg (3.24 mmol) of 5,6-diamino-1-propyluracil (Japanese Published Unexamined Patent Application No. 173889/91). The obtained crude product was purified by silica gel column chromatography (eluent: 10% methanol/chloroform) to give 923 mg (yield: 82%) of a ca. 1:4 mixture of 6-amino-5-(9-oxo-3-tricyclo[3.3.1.0³,⁷]nonylcarbonylamino)-1-propyluracil (Compound K) and 6-amino-5-(6-oxo-3-tricyclo[3.3.1.0³,⁷]nonylcarbonylamino) -1-propyluracil (Compound L) as a white powder.

Melting Point: 269.6°–272.2° C. IR(KBr) $\nu_{max}$ (c⁻¹): 1738, 1698, 1640, 1582, 1493. MS(EI) m/e: 346(M+).

Substantially the same procedure as in Example 3 was repeated using 920 mg (2.66 mmol) of a ca. 1:4 mixture of Compound K and Compound L, and 101 mg (2.66 mmol) of sodium borohydride. The obtained crude product was purified by silica gel column chromatography (eluent: 20% methanol/chloroform) to give 698 mg (yield: 75%) of a ca. 1:1:8 mixture of 6-amino-5-(trans-9-hydroxy-3-tricyclo[3.3.1.0³,⁷]nonylcarbonylamino)-1-propyluracil (Compound M), 6-amino-5-(cis-9-hydroxy-3-tricyclo[3.3.1.03,7]nonylcarbonylamino)-1-propyluracil (Compound N) and 6-amino-5-(trans-6-hydroxy-3-tricyclo[3.3.1.0³,⁷]nonylcarbonylamino)-1-propyluracil (Compound O) as a white powder.

Melting Point: 278.8°–290.2° C. IR(KBr) $\nu_{max}$ (cm⁻¹): 1695, 1612, 1486. MS(EI) m/e: 348(M+).

Substantially the same procedure as in Reference Example 3 was repeated using 696 mg (1.98 mmol) of a ca. 1:1:8 mixture of Compound M, Compound N and Compound O. The obtained crude product was purified by silica gel column chromatography (eluent: 10% methanol/chloroform) to give 208 mg (yield: 26%) of a ca. 1:1:8 mixture of Compound P, Compound Q and Compound R as a white powder.

Melting Point: 120.7°–123.2° C. IR(KBr) $\nu_{max}$ (cm⁻¹): 1730(sh), 1699, 1638, 1484. MS(EI) m/e: 404 (M+).

What is claimed is:

1. A xanthine compound represented by the formula (I)

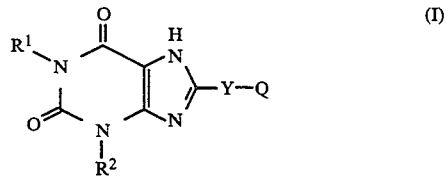

wherein R¹ and R² are the same or different and each represent hydroxy-substituted, oxo-substituted or unsubstituted lower alkyl, Y is a single bond or alkylene, and Q is

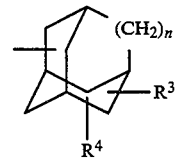

(wherein R³ and R⁴ are the same or different and each represent hydrogen or hydroxy, n is 0 or 1, and when both R³ and R⁴ are hydrogen, at least one of R¹ and R² is hydroxy-substituted or oxo-substituted lower alkyl), or

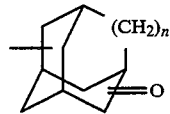

(wherein n has the same meaning as defined above); or a pharmaceutically acceptable salt thereof.

2. The compound according to claim 1, wherein R¹ is hydroxy-substituted, oxo-substituted or unsubstituted propyl; R² is hydroxy-substituted or unsubstituted propyl; and Y is a single bond.

3. The compound according to claim 2, wherein R¹ is propyl, 2-hydroxypropyl, 2-oxopropyl or 3-oxopropyl; R² is propyl, 2-hydroxypropyl or 3-hydroxypropyl.

4. The compound according to any one of claims 1 to 3, wherein Q is 9-hydroxy, 9-oxo or 6-hydroxy substituted 3tricyclo[3.3.1.0³,⁷]nonyl, or 3-hydroxy-1tricyclo[3.3.1.1³,⁷]decyl.

5. The compound according to claim 1, which is selected from the group consisting of 8-(trans-9-hydroxy-3-tricyclo[3.3.1.0³,⁷]nonyl) -1,3-dipropylxanthine, 8-(cis-9-hydroxy-3-tricyclo[3.3.1.0³,⁷]nonyl)-1,3-dipropylxanthine, 8-(trans-9-hydroxy-3-tricyclo[3.3.1.0³,⁷]nonyl)-1-(2-oxopropyl)-3-propylxanthine and 1-(2-hydroxypropyl)-8-(trans-9-hydroxy-3-tricyclo[3.3.1.0³,⁷]nonyl)-3-propylxanthine.

6. A pharmaceutical composition comprising the compound defined by any one of claims 1 to 5 and a pharmaceutically acceptable carrier.

* * * * *

UNITED STATES PATENT AND TRADEMARK OFFICE
CERTIFICATE OF CORRECTION

PATENT NO. : 5,395,836

DATED : March 7, 1995

INVENTORS : JUNICHI SHIMADA ET AL.

Page 1 of 4

It is certified that error appears in the above-identified patent and that said Letters Patent is hereby corrected as shown below:

ON THE TITLE PAGE

At [56] References Cited

Under "U.S. PATENT DOCUMENTS"

"Suzuki" should read --Suzuki et al.--.

At [57] ABSTRACT

Line 4, "represent" should read --represents--.

COLUMN 4

Line 35, "above.)" should read --above).--.
Line 44, "ing." should read --ing:--.
Line 57, "ing." should read --ing:--.

COLUMN 6

Line 60, "water;" should read --water--.

COLUMN 9

Line 30, "above)" should read --above).--.

COLUMN 15

Line 65, "(manufacture" should read --(manufactured--.

UNITED STATES PATENT AND TRADEMARK OFFICE
CERTIFICATE OF CORRECTION

PATENT NO. : 5,395,836

DATED : March 7, 1995

INVENTORS : JUNICHI SHIMADA ET AL.

It is certified that error appears in the above-identified patent and that said Letters Patent is hereby corrected as shown below:

COLUMN 18

TABLE 5, "uria" should read --urea--.
TABLE 5, "t test);[1)]" should read ----t-test);1)--
    and "test);[2)]" should read --test);2)--.
Line 50, "(1990)]" should read --(1990)].--.

COLUMN 19

TABLE 6, "used animals" should read --animals used--.

COLUMN 21

Line 2, "″max(cm$^{-1}$):" should read --$\nu_{max}$(cm$^{-1}$):--.
Line 14, "-3tricyclo" should read --3-tricyclo--.

COLUMN 23

Line 18, "(3tricyclo" should read --3-tricyclo--.
Line 45, "$\nu_{max}$(c$^{-1}$):" should read --$\nu_{max}$(cm$^{-1}$):--.
Line 55, "$\nu_{max}$(c$^{-1}$):" should read --$\nu_{max}$(cm$^{-1}$):--.
Line 58, "2.78(1  H," should read --2.78(1H,-- and
    --J=6.5  Hz)," should read --J=6.5Hz),--.
Line 59, "J=7.4  Hz)" should read --J=7.4Hz).--.

COLUMN 24

Line 30, "(c$^{-1}$):" should read --(cm$^{-1}$):--.
Line 67, "(c$^{-1}$):1703," should read --(cm$^{-1}$):1703,--.

UNITED STATES PATENT AND TRADEMARK OFFICE
CERTIFICATE OF CORRECTION

PATENT NO. : 5,395,836

DATED : March 7, 1995

INVENTORS : JUNICHI SHIMADA ET AL.

It is certified that error appears in the above-identified patent and that said Letters Patent is hereby corrected as shown below:

COLUMN 26

Line 4, "214.6°-215.7° C" should read --214.6°-215.7°C--.

COLUMN 28

Line 26, "3" should read --3$\ell$--.

COLUMN 29

Line 58, "ice-cooing" should read --ice-cooling--.

COLUMN 30

Line 9, "$\nu_{max}(c^{-1})$:" should read --$\nu_{max}(cm^{-1})$:--.

COLUMN 31

Line 47, "$\nu_{max}(c^{-1})$:" should read --$\nu_{max}(cm^{-1})$:--.

UNITED STATES PATENT AND TRADEMARK OFFICE
CERTIFICATE OF CORRECTION

PATENT NO. : 5,395,836

DATED : March 7, 1995

INVENTORS : JUNICHI SHIMADA ET AL.

It is certified that error appears in the above-identified patent and that said Letters Patent is hereby corrected as shown below:

COLUMN 32

Line 55, "3tricyclo" should read --3-tricyclo-- and "1tricy-" should read --1-tricy- --.

Signed and Sealed this

Eighteenth Day of July, 1995

Attest:

BRUCE LEHMAN

Attesting Officer   Commissioner of Patents and Trademarks